(12) United States Patent
Kapoustin et al.

(10) Patent No.: US 10,993,416 B2
(45) Date of Patent: May 4, 2021

(54) SMART AI POWERED ANIMAL BODY HARNESS AND ARMOUR SYSTEM FOR REAL TIME MONITORING OF HUMAN HEALTH AND BEHAVIOUR WHEN WITHIN PROXIMITY TO ANY SUPPORT ANIMAL OR PET

(71) Applicants: Michael Kapoustin, Cape Coral, FL (US); Shem Lachhman, Cape Coral, FL (US); Bojan Vranjes, Cape Coral, FL (US)

(72) Inventors: Michael Kapoustin, Cape Coral, FL (US); Shem Lachhman, Cape Coral, FL (US); Bojan Vranjes, Cape Coral, FL (US)

( * ) Notice: Subject to any disclaimer, the term of this patent is extended or adjusted under 35 U.S.C. 154(b) by 0 days.

(21) Appl. No.: 16/297,758

(22) Filed: Mar. 11, 2019

(65) Prior Publication Data

US 2020/0288673 A1    Sep. 17, 2020

(51) Int. Cl.
*A01K 27/00*      (2006.01)
*A61B 5/00*       (2006.01)
(Continued)

(52) U.S. Cl.
CPC .......... *A01K 27/002* (2013.01); *A01K 27/008* (2013.01); *A01K 29/005* (2013.01);
(Continued)

(58) Field of Classification Search
CPC .............................. A01K 27/002; A01K 15/02
See application file for complete search history.

(56) References Cited

U.S. PATENT DOCUMENTS

2010/0212269 A1*  8/2010  Dell'Agnese ........ A01K 27/006
                                                         54/37.1
2016/0302390 A1* 10/2016  Allen ................... A01K 11/008
(Continued)

*Primary Examiner* — Daniel J Colilla

(57) ABSTRACT

The invention discloses smart Artificial Intelligence powered body harness system for support animals or pets such as a dog and which is capable of real time monitoring of human health, wellbeing, behavior and status of an owner or handler or any of the person of interest within proximity of the equipped support animal or pet. Further, the smart body harness and armor system is capable of monitoring the emotional state and body biometrics and health of the support animals or pet and to transmit in real time the collected data to a centralized monitoring center for AI and human analysis and then reporting on those results to the pet owner and any interested person or organization granted secure access via his/her smartphone or any other network enabled device. The smart body harness system of present invention is comprising of: a flexible body of a harness capable of conforming the body shape of the pet support animals which is further augmented with a network of plurality of electronically connected housings built within the flexible body of harness to support the real time monitoring instruments; each such base stations of the body harness incorporates one or more electronic sensor base plate or mounting platform all of which are networked together as a part of global monitoring network; a plurality of weatherproof, waterproof and shock resistant container having not less than a microcomputer with integrated peripheral devices including but not limited to, a camera, a microphone, a 4G and 5G wireless network components, a Bluetooth module, a Wi-Fi, Battery pack and many more mounted within the base stations of the body harness which acts as a mounting receptacle for the container. Further, each such container has transparent housing for its camera device and each container device is interchangeable with other (Continued)

container device due to the ability of containers to snap-in to the housings via mechanical, magnetic or clip-on mechanisms.

15 Claims, 2 Drawing Sheets

(51) Int. Cl.
*A01K 29/00* (2006.01)
*G06F 3/01* (2006.01)
*H04W 4/38* (2018.01)

(52) U.S. Cl.
CPC .......... *A61B 5/0004* (2013.01); *A61B 5/0026* (2013.01); *G06F 3/011* (2013.01); *H04W 4/38* (2018.02); *A61B 2505/07* (2013.01)

(56) References Cited

U.S. PATENT DOCUMENTS

2016/0337618 A1* 11/2016 Chapman .................. B68C 1/02
2018/0014512 A1* 1/2018 Arabani ................. H04N 7/185

* cited by examiner

SMART AI POWERED ANIMAL BODY HARNESS AND ARMOUR SYSTEM FOR REAL TIME MONITORING OF HUMAN HEALTH AND BEHAVIOUR WHEN WITHIN PROXIMITY TO ANY SUPPORT ANIMAL OR PET

TECHNICAL FIELD

The present invention relates to the body harness cum armor system for emotional support animals such as dog. More particularly, the invention relates to a smart Artificial Intelligence (AI) powered body harness and armor system having integrated biometric sensors and video monitoring devices as part of a real time wireless cloud network for monitoring and reporting on the health, wellbeing and status of the human owner, handler or any person of interest within the proximity of the support animal and also monitoring and reporting on the health and biometrics of the support animal.

BACKGROUND

Support animals and pets, particularly dogs, have for thousands of years been integrated into the fabric of human society and the family. The military, police, emergency responders and rescue teams, agriculture and even medicine have relied on the acute senses, endurance, intelligence, loyalty and empathy that dogs in particular have demonstrated time and time again. Humans also tend to bond for life to their support animals and pets.

However, it is impossible for support animals and pets to communicate information on their surroundings, or on the status and wellbeing of their handlers or even their own state of health. While a support animal may emotionally empathize and witness the distress of its handler or owner, it has no biological tools or enough intelligence to communicate such conditions to a 3rd party and in a meaningful way. Yet, support animals and pets, particularly dogs and their handlers or owners, will form emotional bonds in such a way that they become inseparable. And unlike a human partner, a support animal or pet typically has a single unwavering focus to be in the presence of its human partner.

Therefore, there exists a need of a monitoring and reporting system that can remotely monitor human beings within the same physical space and surroundings shared by a support or pet animal, and to collect data and report on the behavior, state of health and wellbeing of a human handler or any subject human within the proximity of the animal. Further, there is need of a monitoring and reporting system for the animal that can monitor the behavior of the animal and report on its health. Moreover, there is a need for a network and system that wirelessly transmits in real time all collected data on both the human and animal subject to a centralized monitoring center for AI and human analysis and then reporting on those results to an interested party granted secure access via his/her smartphone or any network enabled device.

SUMMARY

This summary is provided to introduce a selection of concepts in a simplified form that are further disclosed in a brief description of the invention. This summary is not intended to identify key or essential inventive concepts of the claimed subject matter, nor is it intended for determining the scope of the claimed subject matter.

The smart AI powered animal body harness and armor system disclosed herein is used for monitoring the health, wellbeing or behavior and status of the animal owner or handler or any person of interest within the proximity of the animal wearing the body harness or armor and transmitting this data via a networked wireless cloud. Further, the smart body harness and armor system is capable of and addresses the above need of a system for real time monitoring of health and behavior of support dogs and emotional support animals or pet animals such as dog or cat and transmitting real time collected data to a centralize monitoring center for AI and human analysis and then reporting on those results to any interested person granted secure access by smart phones or other network handling devices.

According to an embodiment, the smart AI powered body harness and armor system is comprising of: a main body made of a flexible material hence capable of conforming the body shape of animal; a plurality of base stations built within the main body of a harness system each of which incorporates one or more electronic sensor base plate or mounting platforms networked together to form a global monitoring network; a plurality of weatherproof, waterproof and shock resistant containers having not less than a microcomputer with integrated peripheral devices including but not limited to, a camera, a microphone, a 4G and 5G wireless network components, a Bluetooth module, a Wi-Fi, Battery pack and more which is mounted within the base stations of the body harness whereas the base station acts as a mounting receptacle for the container that allows the container to snap-in and out of the base station via simple mechanical, magnetic or clip-on mechanisms.

The principle objective is to provide a smart AI powered animal body harness and armor system that allows support animals to collect and wirelessly communicate information to a global cloud network on their surroundings, the status and wellbeing of their human handlers or any person of interest together with animal's own emotional state of mind or health.

Another objective is to provide a smart AI powered animal body harness and armor system that monitors and transmits real time data on the health of the animal and health of handler, with information on its surrounding etc. to a smartphone or any network enabled device of an owner or any person of interest or monitoring services over a wireless cloud communication network.

Yet another objective is to provide a smart AI powered animal body harness and armor system that monitors 360 degrees around the harnessed or armor equipped animal of all humans within the proximity of the animal.

One more objective is to provide a smart AI powered animal body harness and armor system wherein a plurality of containers of the harness are interchangeable with other similar containers and have the ability to snap-in to the base station via mechanical, magnetic or clip-on mechanism.

Another objective is to provide smart AI powered animal body harness and armor system that is flexible enough to fit and conform body size of the support or pet animal that monitors surrounding as well as protect the animal from injuries.

Yet one objective is to provide a Smart AI powered animal body harness and armor system that is capable of being used in the medical care of human patients as an intelligent platform for harnessed dogs to detect physical distress in any human within observable range undergoing medical care, and to measure the distress level and the integrated AI to alert both the health service providing agency and human monitors nearby.

Yet one more objective is to provide a Smart AI powered animal body harness and armor system that is capable of being used in home health care services to monitor security of a patient, mental or physical abuse of a patient by a caregiver, and prescription drug or other forms of theft.

BRIEF DESCRIPTION OF DRAWINGS

The foregoing summary, as well as the following detailed description of the invention, is better understood when read in conjunction with the appended drawings. For the purpose of mere illustrating of the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF INVENTION

The present invention overcomes the aforesaid drawbacks of the above and other objects, features and advantages of the present invention will now be described in greater detail. Also, the following description includes various specific details and are to be regarded as merely exemplary. Accordingly, those of ordinary skill in the art will recognize that: without departing from the scope and spirit of the present disclosure and its various embodiments there may be any number of changes and modifications described herein.

According to an embodiment, the present invention discloses a smart AI powered animal body harness and armor system for real time monitoring and transmitting of data on the health, behavior and wellbeing of a human handler, owner or any person of interest within the proximity of the animal with the system. Further the system monitors the surroundings of the animal visually using a plurality of cameras along a plurality of biometric sensors measuring health, stress level, activity level, behavior and wellbeing of a human handler or of any person of interest within the proximity of the animal. The system of present embodiment monitors emotional or other support animals or pets such as dogs and any changes in their body biometrics and parameters such as body temperature, respiration rate, hear-beats, sleep activity, activity levels, and calories burned etc. and uses a learning algorithm to associate the sympathetic biological responses in the animal's level of stress to the of that of the animals handler or other person of interest in close proximity.

Figure 1:
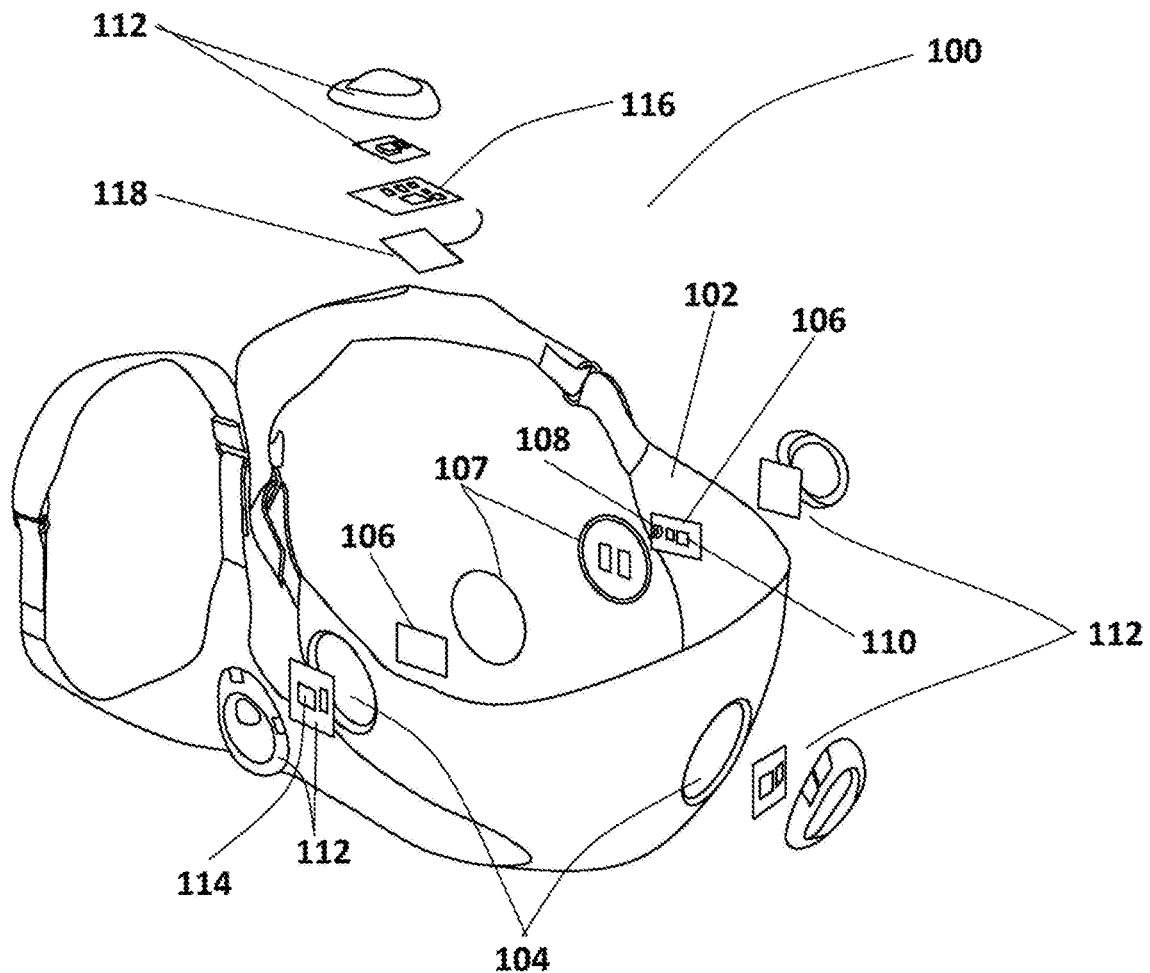
FIG. 1 illustrates exploded view of an exemplary embodiment of the Smart AI Powered Body Harness and Armor System for real time monitoring of the health and behavior of both of the emotional support animal and human owner of the same.

FIG. 1 illustrates exploded view of an exemplary embodiment of the smart AI powered body harness and armor system 100 for support animal 200 (FIG. 2) comprises: a flexible main body 102 of harness 100 having plurality of housings 104 made to configure electronic sensor base plates 106 and electronic container units 112 within the housing 104 which supports and protects electronic monitoring components; a plurality of electronic sensor base plates 106 are configured within the plurality of housings 104 of main body 102 of the harness 100 that further comprises plurality of various sensors to monitor health and behavior of animal; A plurality of container units 112 are also configured within all the plurality of housings 104 to monitor the surroundings of the animal, health of the human handler, behavior of the handler and also to transmit all the data collected in real time to the smartphone, tablet, laptop or any network enabled devices of an owner, handler or any or person of interest such as police, military or medical persons etc.

The main body 102 of the harness or armor system 100 of present invention is made of any of the flexible material such as leather, plastic, rubber or any metal such as aluminum that is capable of protecting electronic components of system as well as capable of acting as an armor for the animal to protect the body of animal. The main body 102 of the armor system covers the Prosternum, Shoulder, Withers, Back and Belly of an animal while the housing 104 are made at plurality of places within the main body 102 so that the monitoring devices enclosed within the housing monitor and cover 306 degrees around the animal.

The electronic sensor base plates 106 of the system 100 is comprising of plurality of biometric sensors 108 that measures and monitors heart-rate, body temperature, respiration rate and other biometrics of the animal body. The electronic sensor base plate 106 further comprises an accelerometer 110 that tracks activity levels, calories burned and sleep activity of animal body to monitor behavior of emotional support animals.

According to present embodiment, the container unit 112 is made up of two components namely electronic plate with all the electronic components and a transparent enclosure housing that allows monitoring by cameras 114 of electronic plate which are shown as exploded in exemplary embodiment of FIG. 1. The electronic plate of container units 112 are further comprising of a microprocessor communicatively coupled with all other electronic base plates and container units 112 within the body 102 of harness 100 to collect all the real time data coming from sensors and other monitoring instruments and transmits the collected real time data to the network enabled user devices using the wireless network devices 116 and cloud server. A plurality of wide-angle infrared cameras 114 are placed within the container unit 112 that visually monitors and records real time events happening around animal and behavior or wellbeing of handler etc. in both daytime and night time.

The container units 112 of the system 100 further comprises a microphone (not shown) for audio monitoring of environment around animal; a plurality of thermodynamic sensors (not shown) to monitor and ensure safety of the human handler or owner within the proximity of animal, to monitor health, stress level and activity levels of human owner or handler around the animal; a wireless networking and communication devices and modules 116; a Bluetooth and a Wi-Fi modules that allows the system to transmit the real time data from any remote location to the network enabled device or devices of any interest person such as the human owner or handler, family members of the human owner, police, military or any health providers via a secure wireless network and cloud processing platform. The system 100 further comprises a rechargeable battery units 118 that provides power for working of all the electronic components of system. Further, the container units 112 of the system 100 are capable of interchanging it with other similar container units 112 due to the ability of the container units 112 to snap-in to the housings via mechanical, magnetic or clip-on mechanisms.

Figure 2:
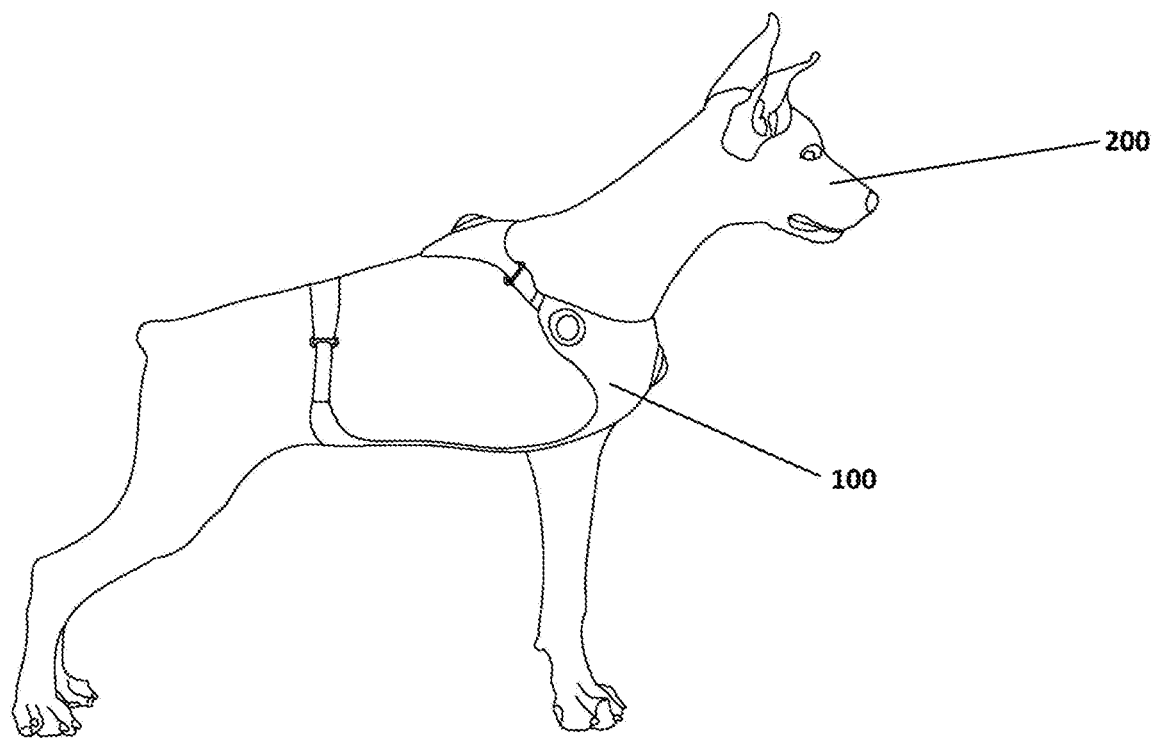
FIG. 2 shows an emotional support animal which is hereby a dog with Smart AI powered body harness and armor system on its body.

Now, FIG. 2 exemplarily illustrates support animal or pet 200 which is hereby dog with Smart AI powered body harness and armor system 100 affixed on the body of the dog. Support or pet animals 200 are not limited to dogs only and it can be any of other animal such as cat. The armor system 100 of present invention, is capable to conform body of various support or pet animals 200 as it comprises plurality of slings with adjusting and locking mechanism that allows conforming of body armor 100 on various sized animals 200.

The invention claimed is:

1. A smart AI powered animal body harness and armor system for a support animal comprising:
    a flexible body of harness with a plurality of housings for supporting and protecting electronic components of the system;
    a plurality of electronic sensor base plates configured within each of the housings of the flexible body of harness; and
    a waterproof, weatherproof and shock resistant container unit configured within each of the housings of the body harness, each said container unit of which further comprises:
        a microprocessor;
        a wide angle camera;
        a microphone;
        a thermodynmaic sensors;
        a wireless networking module;
        a Bluetooth module;
        a Wi-Fi module; and
        a battery unit.

2. The smart AI powered animal body harness and armor system of claim 1, wherein the flexible body of harness works as an armor for the support animal wherein said armor covers and protects the prosternum, the shoulders, the withers, the back, and the belly of the support animal.

3. The smart AI powered animal body harness and armor system of claim 1, wherein the body of harness further comprises plurality of slings with locking mechanisms that allows the support animal to wear the body of harness.

4. The smart AI powered animal body harness and armor system of claim 1, wherein each of the electronic base plates comprises a plurality of biometric sensors for monitoring and recording biometrics such as body temperature, heartbeat, and respiration rate to monitor the health of the support animal.

5. The smart AI powered animal body harness and armor system of claim 1, wherein each of the electronic base plates comprises an accelerometer to track activity levels, calories burned and sleep activity of the support animal.

6. The smart AI powered animal body harness and armor system of claim 1, wherein the container units are configured to monitor the surroundings of the support animal as well as health, wellbeing and behavior of a handler or any person of interest within proximity of the support animal.

7. The smart AI powered animal body harness and armor system of claim 1, wherein the plurality of housings and hence the plurality of container units are placed at locations including the shoulders, the prosternum and the back of animal to allow 360 degree monitoring.

8. The smart AI powered animal body harness and armor system of claim 1, wherein each container unit of plurality of container units is interchangeable with other similar container units by snapping-out and snapping-in into a respective housing via a mechanical, magnetic or clip-on mechanism.

9. The smart AI powered animal body harness and armor system of claim 1, wherein the housing of each container unit is transparent for the camera device located in the respective container unit.

10. The smart AI powered animal body harness and armor system of claim 1, wherein the thermodynamic sensors of each container unit are configured to monitor health, stress level, activity level and to ensure safety of a handler or any person of interest, within the proximity of the support animal.

11. The smart AI powered animal body harness and armor system of claim 1, wherein the system transmits collected data to a client device, such as a smartphone, laptop, tablet, PC or any network enabled device using wireless networking.

12. The smart AI powered animal body harness and armor system of claim 1, wherein the system is configured to collect data from a cloud network for the purpose of making reports to any of police, military, healthcare providers and family members of a handler of the support animal.

13. A method of working of a Smart AI powered animal body harness and armor system comprises steps of:
    providing said animal body harness and armor system with a plurality of thermal graphic sensors and a plurality of infrared imaging cameras;
    fixing the harness system on the body of a support animal;
    initiating working of the system wirelessly using any registered network enabled device of an owner of the system or any registered network enabled device of any person of interest;
    monitoring and analyzing, with said system, body health data, distress and activity level data and other body biometric data of the support animal in real time;
    utilizing analyzed data of the support animal to establish a state of health and wellbeing of a human handler within the proximity of the system;
    determining body temperature data, heart rate data and blood pressure data of the human handler or the owner within the proximity of the support animal using said thermal graphic sensors of the system;
    assessing health, emotional state, activity and stress levels, behavior or wellbeing of the human handler or the owner or any other person surrounding the human owner within the proximity of support animal;
    determining a real time location data of the human handler or the owner;
    surveilling a surrounding environment using said plurality of infrared imaging cameras of the system in a daytime and a night time thereby creating surveillance image data;
    collecting and transmitting all the monitored, determined, and surveillance data in real time to a network enabled, personal device, and transmitting, via a wireless cloud network the owner or family of the owner or any other person of interest such as police, military, medical personnel or any other security persons.

14. The method of working of the Smart AI powered animal body harness and armor system of claim 13 further comprises step of:
    comparing real time collected data of the support animal's body health, body stress and activity level, and behavior with predefined threshold limits; and
    comparing real time collected data of the human handler's or owner's body health, activity and stress level, and behavior with predefined threshold limits.

15. The method of working of the Smart AI powered animal body harness and armor system of claim 14 further comprising a step of: sending alert signals to concerned persons and authorities in a case of any data crossing a respective one of said predefined threshold limits.

* * * * *